United States Patent
Frantz

(10) Patent No.: US 9,482,706 B2
(45) Date of Patent: Nov. 1, 2016

(54) METHODS AND CIRCUITS FOR MEASURING A HIGH IMPEDANCE ELEMENT BASED ON TIME CONSTANT MEASUREMENTS

(71) Applicant: Dust Company, Inc., Raleigh, NC (US)

(72) Inventor: Frederick E. Frantz, Raleigh, NC (US)

(73) Assignee: Dust Company, Inc., Raleigh, NC (US)

( * ) Notice: Subject to any disclaimer, the term of this patent is extended or adjusted under 35 U.S.C. 154(b) by 939 days.

(21) Appl. No.: 13/710,896

(22) Filed: Dec. 11, 2012

(65) Prior Publication Data
US 2014/0159747 A1    Jun. 12, 2014

(51) Int. Cl.
  *G01R 27/26* (2006.01)
  *G01N 27/60* (2006.01)
  *G01R 27/02* (2006.01)

(52) U.S. Cl.
  CPC ............. *G01R 27/26* (2013.01); *G01N 27/60* (2013.01); *G01R 27/025* (2013.01)

(58) Field of Classification Search
  CPC ..... G01R 27/26; G01R 27/025; G01N 27/60
  USPC .................................................. 324/677–684
  See application file for complete search history.

(56) References Cited

U.S. PATENT DOCUMENTS

| | | | | |
|---|---|---|---|---|
| 5,287,061 A | * | 2/1994 | Dechene | G01N 27/60 324/454 |
| 5,371,469 A | * | 12/1994 | Anderson | G01D 18/00 324/130 |
| 5,514,976 A | * | 5/1996 | Ohmura | G01R 31/31924 324/762.01 |
| 5,657,238 A | * | 8/1997 | Lindeboom | G01K 7/24 324/677 |
| 6,191,723 B1 | | 2/2001 | Lewis | |
| 2003/0001608 A1 | * | 1/2003 | Thibeault | G01R 31/3004 324/762.02 |
| 2003/0030451 A1 | | 2/2003 | Braun | |
| 2003/0089159 A1 | | 5/2003 | Roe | |
| 2003/0151418 A1 | * | 8/2003 | Leger | G01R 31/006 324/715 |
| 2006/0250152 A1 | * | 11/2006 | Rius Vazquez | G01R 31/3008 324/750.3 |
| 2006/0267599 A1 | | 11/2006 | Pooranakaran et al. | |
| 2014/0203824 A1 | * | 7/2014 | Nivet | G01N 27/221 324/663 |

FOREIGN PATENT DOCUMENTS

| | | |
|---|---|---|
| DE | 3642861 A1 | 6/1988 |
| DE | 4420998 A1 | 12/1995 |
| DE | 19546304 A1 | 6/1997 |

OTHER PUBLICATIONS

Notification of Transmittal of the International Search Report and the Written Opinion of the International Searching Authority, or the Declaration, in corresponding PCT Application No. PCT/US2013/074266, mailed Mar. 17, 2014 (11 pages).

* cited by examiner

*Primary Examiner* — Farhana Hoque
(74) *Attorney, Agent, or Firm* — Myers Bigel & Sibley

(57) ABSTRACT

A method of measuring impedance includes determining a first time constant based on a known impedance and a capacitor, determining a second time constant based on a target impedance and the capacitor, and determining the target impedance based on the first time constant and the second time constant.

16 Claims, 6 Drawing Sheets

METHODS AND CIRCUITS FOR MEASURING A HIGH IMPEDANCE ELEMENT BASED ON TIME CONSTANT MEASUREMENTS

BACKGROUND

The present invention relates to electrical circuit element measurement technology, and, more particularly, to methods and circuits for measuring high impedance elements.

Many electrical circuits require a high level of isolation for electrical components to ensure that these components aren't adversely affected by short circuits, electrical fields, magnetic fields, and the like. FIG. 1 illustrates an example where electrical isolation of measurement circuit components is important to obtain valid data. In particular, FIG. 1 is a diagram that illustrates circuitry for evaluating the concentration of particulate in a gas stream. A stack 105 has a gas that flows therethrough and contains particulate matter 110. A probe 115 is configured to extend into the gas stream and is charged through a triboelectric effect by the particulate matter 110 colliding with the probe 115. The triboelectric effect results in an signal being generated, which can be processed by signal processing circuitry 120 and provided as an input to a particulate matter analysis module 125 to evaluate the concentration of the particulate 110 matter in the gas stream.

The particulate matter 110 in the gas stream along with dust and other foreign debris can build up on surfaces of the stack 105 and/or the probe 115 and have the potential to affect the electrical characteristics of the probe 115. For example, build-up of debris adjacent to the probe 115 may create electrical paths to ground or other electrical circuits resulting in a signal output from probe 115 that is not representative of the concentration of the particulate matter 110 in the gas stream.

SUMMARY

According to some embodiments of the present invention, a method of measuring impedance comprises determining a first time constant based on a known impedance and a capacitor, determining a second time constant based on a target impedance and the capacitor, and determining the target impedance based on the first time constant and the second time constant.

In other embodiments, determining the first time constant comprises driving a test circuit comprising the known impedance and the capacitor connected in series with a first test voltage.

In still other embodiments, the first test voltage is in a range from about 0V to about 3.3V.

In still other embodiments, the known impedance has a value is in a range from about 1 megaohm to about 10 megaohms.

In still other embodiments, wherein the capacitor has a value in a range from about 1 nanofarad to about 10 nanofarads.

In still other embodiments, determining the first time constant further comprises charging the capacitor with the first test voltage and determining a time taken to charge the capacitor to a threshold voltage level.

In still other embodiments, wherein determining the first time constant further comprises charging the capacitor to a known voltage level, discharging the capacitor through the known impedance, and determining a time taken for the capacitor voltage level to decrease to a threshold voltage level.

In still other embodiments, determining the second time constant comprises, replacing the known impedance in the test circuit with the target impedance and driving the test circuit comprising the target impedance and the capacitor connected in series with a second test voltage.

In still other embodiments, the first and second test voltages are the same.

In still other embodiments, the first and second test voltages are different.

In still other embodiments, the second test voltage is in a range from about 0V to about 24V.

In still other embodiments, the target impedance has a value is in a range from about 10 megaohms to about 50 megaohms.

In still other embodiments, determining the second time constant further comprises charging the capacitor with the second test voltage and determining a time taken to charge the capacitor to a threshold voltage level.

In still other embodiments, determining the second time constant further comprises charging the capacitor to a known voltage level, discharging the capacitor through the target impedance, and determining a time taken for the capacitor voltage level to decrease to a threshold voltage level, In still other embodiments, the target impedance comprises an electrical path between a triboelectric probe and a common node.

In still other embodiments, the triboelectric probe is disposed in a gas stream containing particulate matter.

In further embodiments of the present invention, an impedance measurement circuit comprises a test circuit comprising a capacitor connected to a test voltage and a controller that is configured to switch a known impedance in series with the capacitance and the test voltage to determine a first time constant based on the known impedance and the capacitor, to a target impedance in series with the capacitance in place of the known impedance to determine a second time constant based on the target impedance and the capacitor, and to determine the target impedance based on the first time constant and the second time constant.

In still further embodiments, the controller is further configured to determine the first time constant by charging the capacitor with the test voltage. The impedance measurement circuit further comprises a voltage comparator that is configured to determine when the capacitor is charged to a threshold voltage level and a timer that is configured to determine a time taken to charge the capacitor to the threshold voltage level.

In still further embodiments, the controller is further configured to determine the second time constant by charging the capacitor with the test voltage. The impedance measurement circuit further comprises a voltage comparator that is configured to determine when the capacitor is charged to a threshold voltage level and a timer that is configured to determine a time taken to charge the capacitor to the threshold voltage level.

In still other embodiments of the present invention, a computer program product for measuring an impedance comprises a non-transitory computer readable medium comprising computer readable program code thereon. The computer readable program code comprises computer readable program code configured to determine a first time constant based on a known impedance and a capacitor, computer readable program code configured to determine a second time constant based on a target impedance and the capacitor, and computer readable program code configured to determine the target impedance based on the first time constant and the second time constant.

BRIEF DESCRIPTION OF THE DRAWINGS

Other features of the present invention will be more readily understood from the following detailed description of specific embodiments thereof when read in conjunction with the accompanying drawings, in which.

DETAILED DESCRIPTION OF EMBODIMENTS

Figure 1:
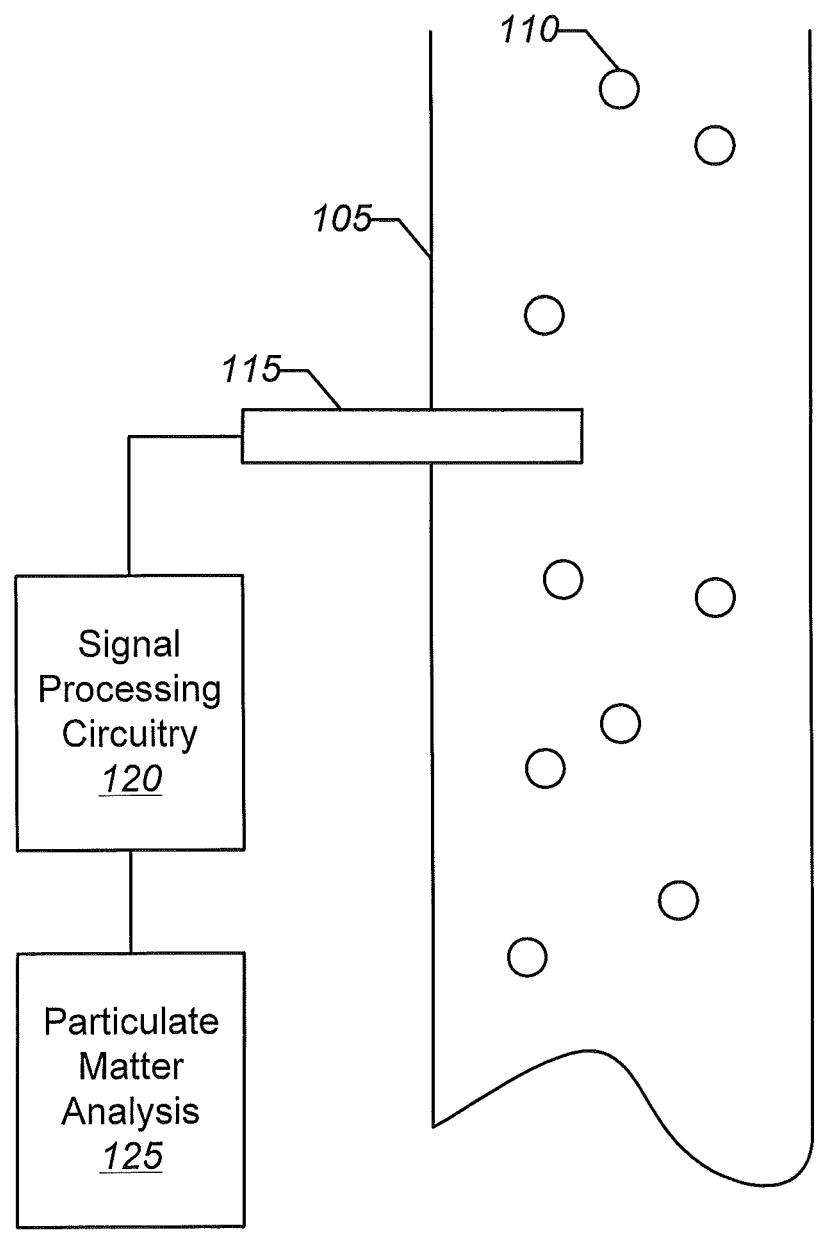
FIG. 1 is a diagram that illustrates circuitry for evaluating the concentration of particulate in a gas stream.

While the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention as defined by the claims. Like reference numbers signify like elements throughout the description of the figures.

As used herein, the singular forms "a," "an," and "the" are intended to include the plural forms as well, unless expressly stated otherwise. It should be further understood that the terms "comprises" and/or "comprising" when used in this specification is taken to specify the presence of stated features, integers, steps, operations, elements, and/or components, but does not preclude the presence or addition of one or more other features, integers, steps, operations, elements, components, and/or groups thereof. It will be understood that when an element is referred to as being "connected" or "coupled" to another element, it can be directly connected or coupled to the other element or intervening elements may be present. Furthermore, "connected" or "coupled" as used herein may include wirelessly connected or coupled. As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and this specification and will not be interpreted in an idealized or overly formal sense unless expressly so defined herein.

For purposes of illustration, embodiments of the present invention are described herein in the context of measuring the impedance of a triboelectric probe relative to a reference node voltage (e.g., ground) to ensure that the probe is sufficiently electrically isolated to generate a signal indicative of particulate matter concentration in a gas stream. It will be understood, however, that the present invention is not limited to such embodiments and may be embodied generally as an impedance measurement circuit for high impedance applications.

Conventional impedance measurement circuits for high impedance elements may use high voltages to generate sufficient current through the high impedance element that can be measured to calculate the impedance value. Such voltages can be dangerous or may be disallowed due to safety regulations for some applications. According to some embodiments of the present invention, a target impedance can be measured based on time constant determinations of a capacitive circuit with both a known impedance and the target impedance. Because the time constant measurements are independent of the voltage used to drive the capacitive circuit, high voltages can be avoided providing a safer methodology for measuring the target impedance.

Figure 2:
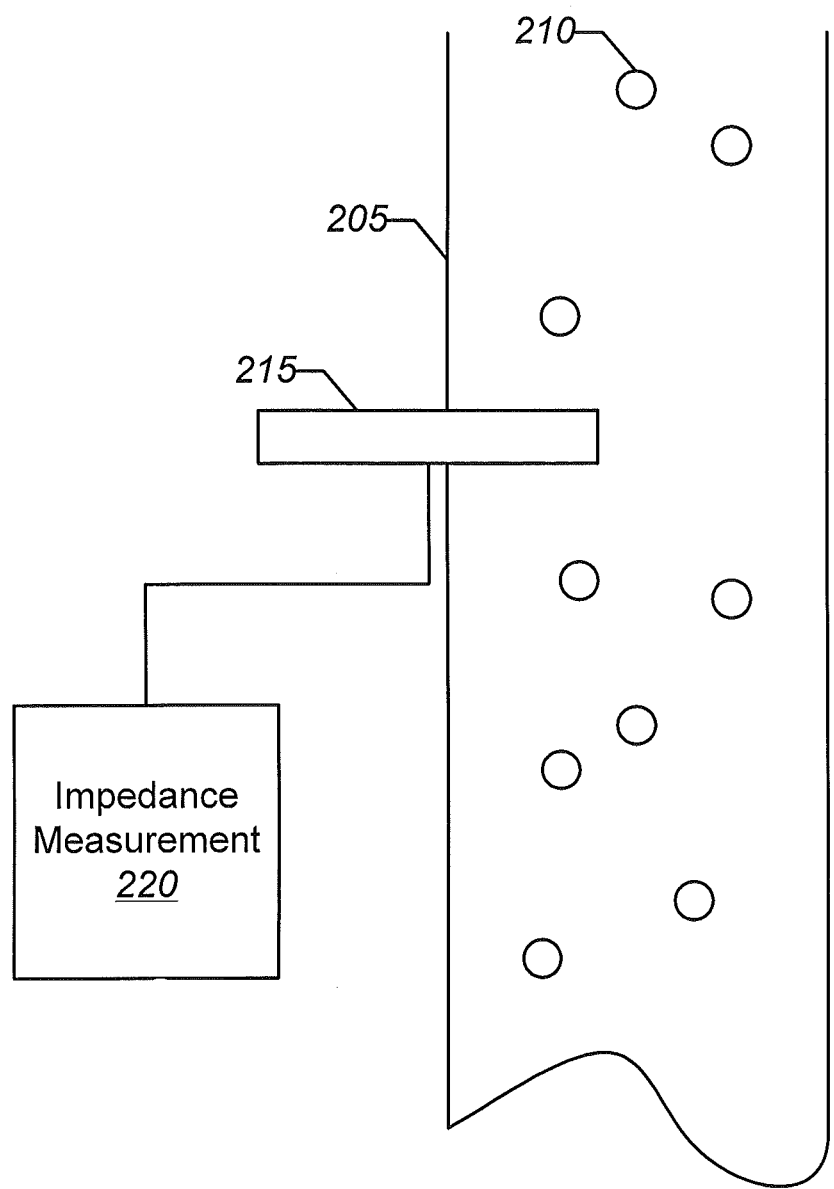
FIG. 2 illustrates an application for measuring a target impedance using an impedance measurement circuit according to some embodiments of the present invention.

FIG. 2 illustrates an application for measuring a target impedance using an impedance measurement circuit according to some embodiments of the present invention. In particular, FIG. 2 is similar to FIG. 1 and illustrates circuitry for evaluating the concentration of particulate in a gas stream. A stack 205 has a gas that flows therethrough and contains particulate matter 210. A probe 215 is configured to extend into the gas stream and is charged through a triboelectric effect by the particulate matter 210 colliding with the probe 215. The triboelectric effect results in a signal being generated, which can be processed to evaluate the concentration of the particulate 210 matter in the gas stream as described above. Further, as described above, build-up of debris adjacent to the probe 215 may create electrical paths to ground or other electrical circuits resulting in a signal output from probe 215 that is not representative of the concentration of the particulate matter 210 in the gas stream. The impedance measurement circuit 220, according to some embodiments of the present invention, may be connected to the probe 215 to measure a target impedance between the probe 215 and ground or another reference node based on time constant determinations.

Figure 3:
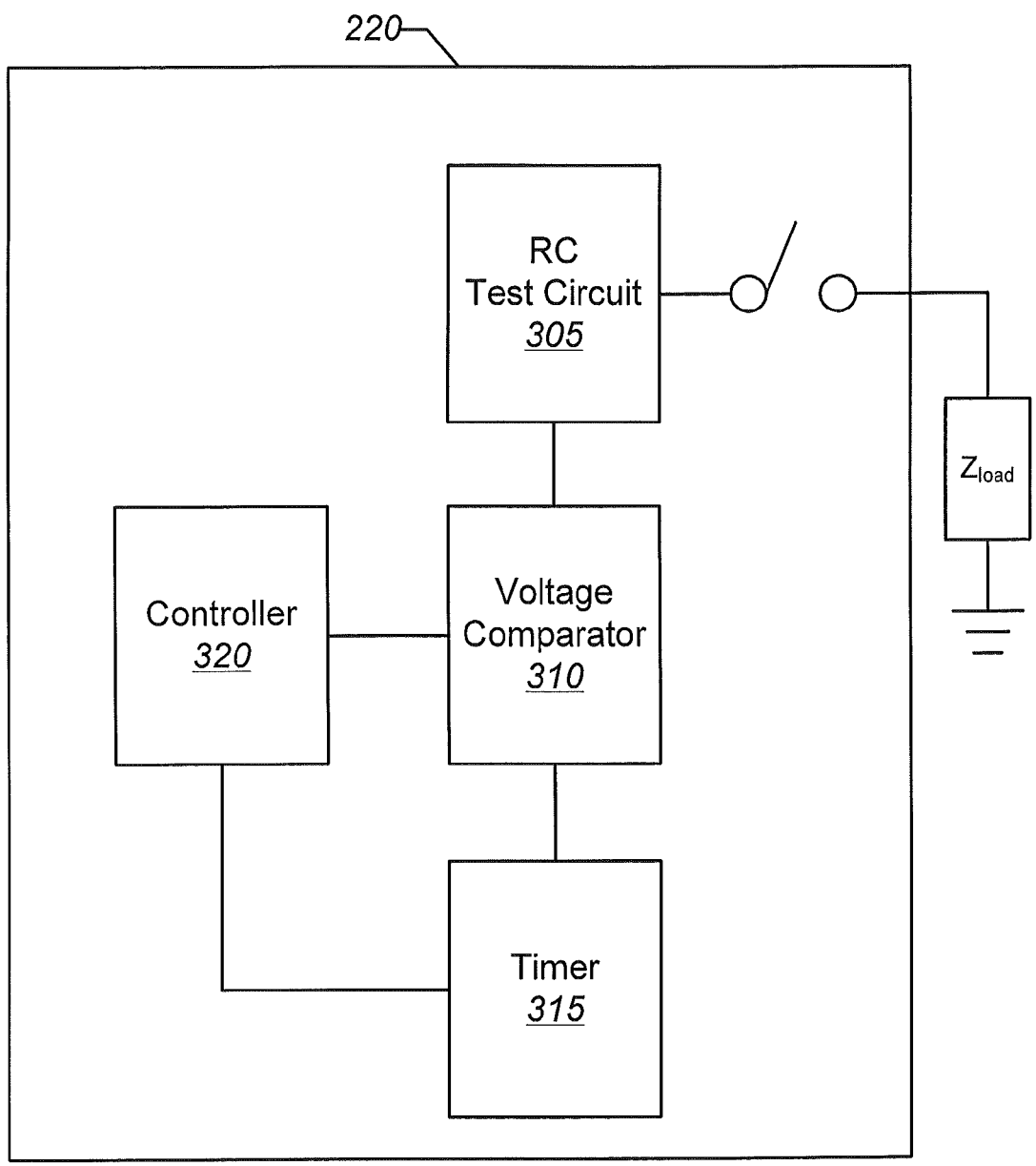
FIG. 3 is a block diagram of the impedance measurement circuit FIG. 2 according to some embodiments of the present invention.

FIG. 3 is a block diagram of the impedance measurement circuit 220 of FIG. 2 according to some embodiments of the present invention. The impedance measurement circuit 220 comprises an RC test circuit 305, a voltage comparator 310, a timer 315, and a controller 320, which are connected as shown. A target impedance to be measured, which is identified as $Z_{load}$, can be switched into the RC test circuit 305 for determining a time constant based on the target impedance. The voltage comparator 310 and the timer 315 are configured to determine a time for a voltage to reach a specific threshold level in the RC test circuit 305 to obtain a time constant value. The controller 320 is configured to coordinate the operations of the other components of the impedance measurement circuit 220 including switches and to process the data from the timer and 315 and known circuit element values from the RC test circuit 305 to determine the value of the target impedance $Z_{load}$.

Figure 4:
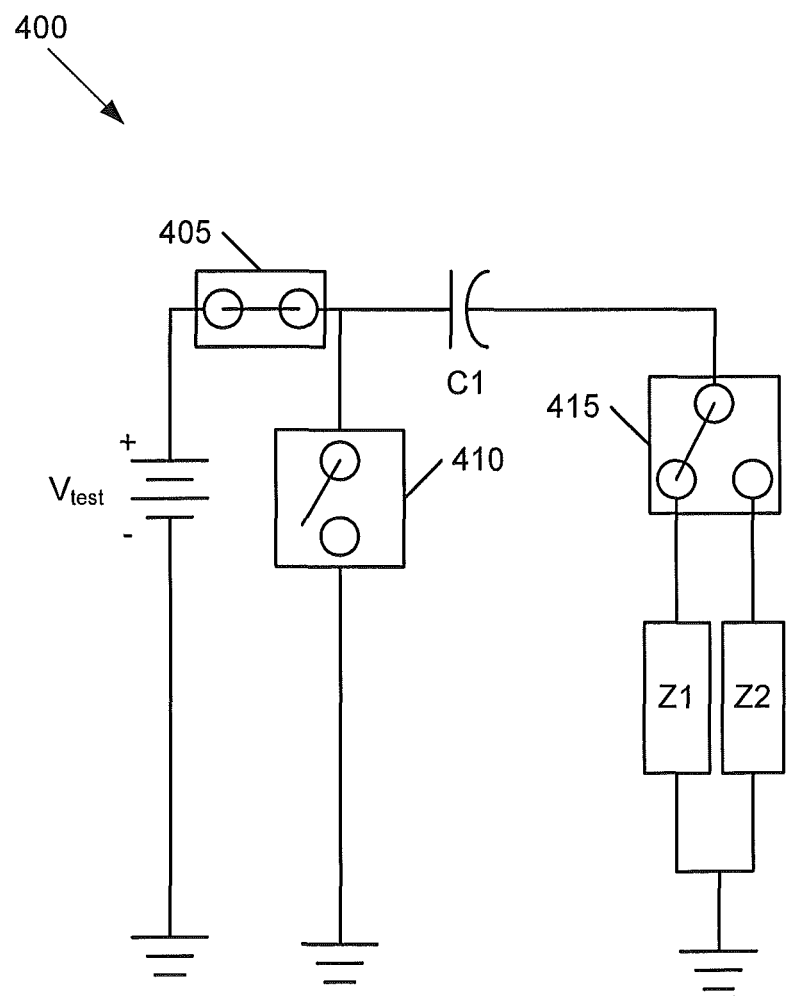
FIG. 4 is a schematic of the RC test circuit of FIG. 3 according to some embodiments of the present invention.
Figure 5:
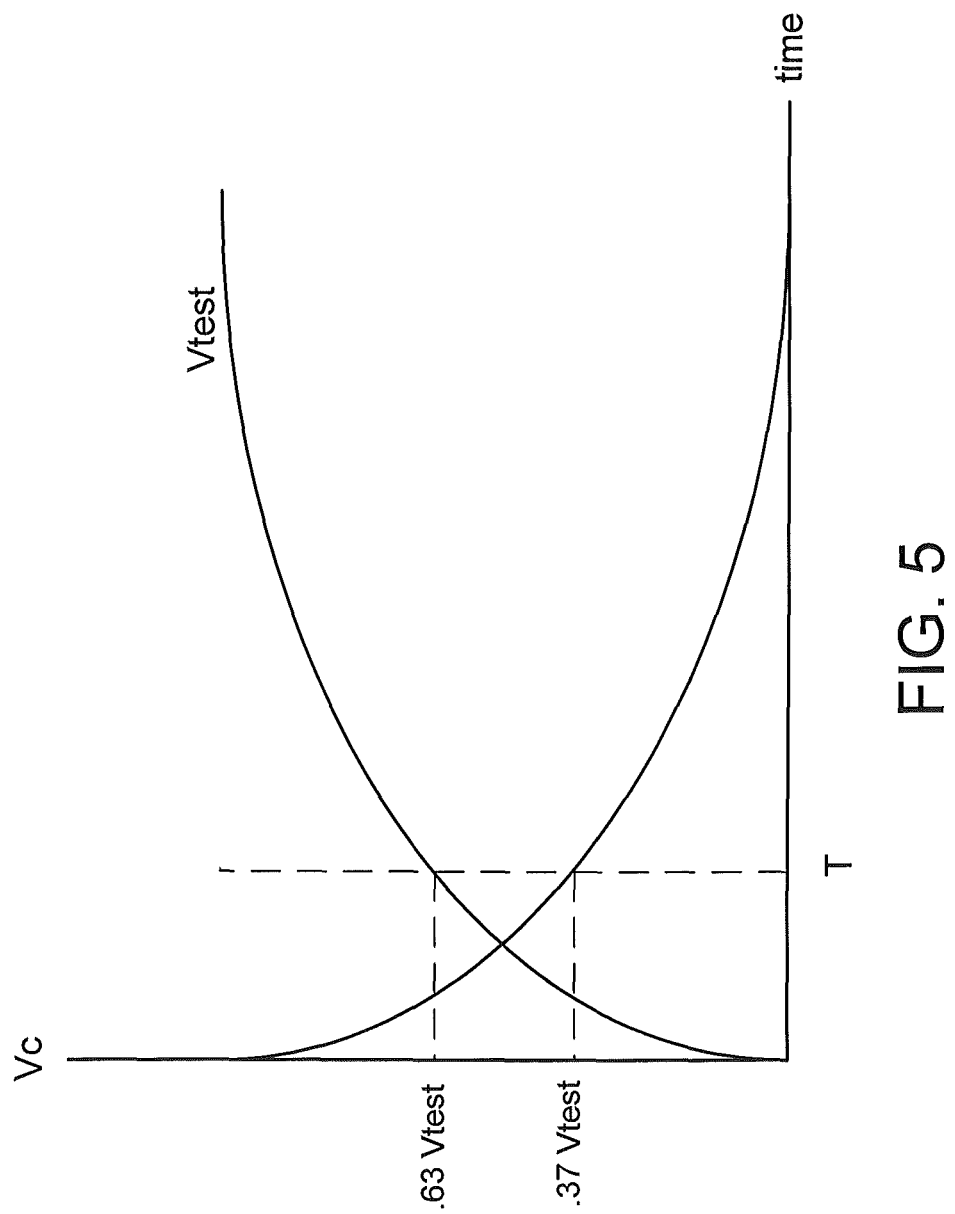
FIG. 5 is a graph showing capacitor charge and discharge curves according to some embodiments of the present invention.

FIG. 4 is a schematic of the RC test circuit 305 of FIG. 3 according to some embodiments of the present invention. The RC test circuit schematic 400 includes a capacitor C1 that can be coupled to one of two impedance elements Z1 or Z2 via switches 405 and 415. For example, impedance element Z1 may be a known impedance value while impedance value Z2 may be a target impedance whose value is unknown. Thus, the switch 405 may be closed and the switch 415 may be used to select the known impedance element Z1 to charge the capacitor C1 with the voltage Vtest. This operation may be performed to confirm the time constant based on the known circuit elements of C1 and Z1. As shown in FIG. 5, the capacitor C1 charges at a rate such that the voltage across capacitor C1 is 63% of the charging voltage Vtest at a time T corresponding to one time constant. Thus, the controller 320 may activate the timer circuit 315 when switches 405 and 415 are activated and the voltage comparator 310 of FIG. 1 may determine when the voltage across the capacitor C1 reaches 63% of the drive voltage Vtest. The timer circuit 315 may then be deactivated and the time recorded, which is equal to one time constant T. This value may be used to confirm the accuracy of the values of the known components C1 and Z1, i.e., the time constant T may be compared to the product of C1 and Z1. The controller 320 may then discharge the capacitor C1 by opening the switch 405 and closing the switch 410. Similar operations may then be performed for the target impedance Z2 whose impedance value is unknown by closing the switch 405 and selecting impedance element Z2 with switch 415.

It will be understood that the time constant determinations for the RC circuits comprising C1-Z1 and C2-Z2 may also be performed by charging the capacitor C1 to the Vtest drive voltage value and then opening switch 405 and closing switch 410 at which time the timer circuit 315 is activated. The voltage comparator 315 may then determine when the voltage across the capacitor reaches 37% of the drive voltage Vtest as shown in FIG. 5. The timer circuit 315 is then deactivated and the time recorded, which is equal to one time constant.

In accordance with various embodiments of the present invention, the voltage threshold used for deactivating the timer circuit 315 may selected for convenience and ease of detection with the time constant being determined according to the time along the exponential curves of FIG. 5 that the voltage threshold is reached. As the time constant is independent of the value of driving voltage Vtest, a voltage may be selected for Vtest that provides a desired level of safety and is suitable for the voltage comparator 310. In addition, Vtest may be set to different values when determining the time constants for the known impedance Z1 and the target impedance Z2 or Vtest may be set to the same voltage level for both time constant determinations.

In accordance with some embodiments of the present invention, the capacitor C1 may have a value in a range from about 1 nanofarads to about 10 nanofarads. The known impedance Z1 may have a resistance value in a range from about 1 megaohm to about 10 megaohms. The voltage Vtest used to determine the time constant for C1 and Z1 may have a voltage value in a range from about 0V to about 3.3V. The voltage Vtest used to determine the time constant for C1 and the target impedance Z2 may have a voltage value in a range from about 0V to about 24V.

The present invention is described herein with reference to flowchart, information flow, and/or block diagram illustrations of methods, systems, and computer program products in accordance with exemplary embodiments of the invention. These flowchart, information flow, and/or block diagrams further illustrate exemplary operations for measuring impedance, in accordance with some embodiments of the present invention. It will be understood that each block of the flowchart, information flow, and/or block diagram illustrations, and combinations of blocks in the flowchart, information flow, and/or block diagram illustrations, may be implemented by computer program instructions and/or hardware operations. These computer program instructions may be provided to a processor of a general purpose computer, a special purpose computer, or other programmable data processing apparatus to produce a machine, such that the instructions, which execute via the processor of the computer or other programmable data processing apparatus, create means and/or circuits for implementing the functions specified in the flowchart and/or block diagram block or blocks.

These computer program instructions may also be stored in a computer usable or computer-readable memory that may direct a computer or other programmable data processing apparatus to function in a particular manner, such that the instructions stored in the computer usable or computer-readable memory produce an article of manufacture including instructions that implement the function specified in the flowchart, information flow, and/or block diagram block or blocks.

The computer program instructions may also be loaded onto a computer or other programmable data processing apparatus to cause a series of operational steps to be performed on the computer or other programmable apparatus to produce a computer implemented process such that the instructions that execute on the computer or other programmable apparatus provide steps for implementing the functions specified in the flowchart, information flow, and/or block diagram block or blocks.

Figure 6:
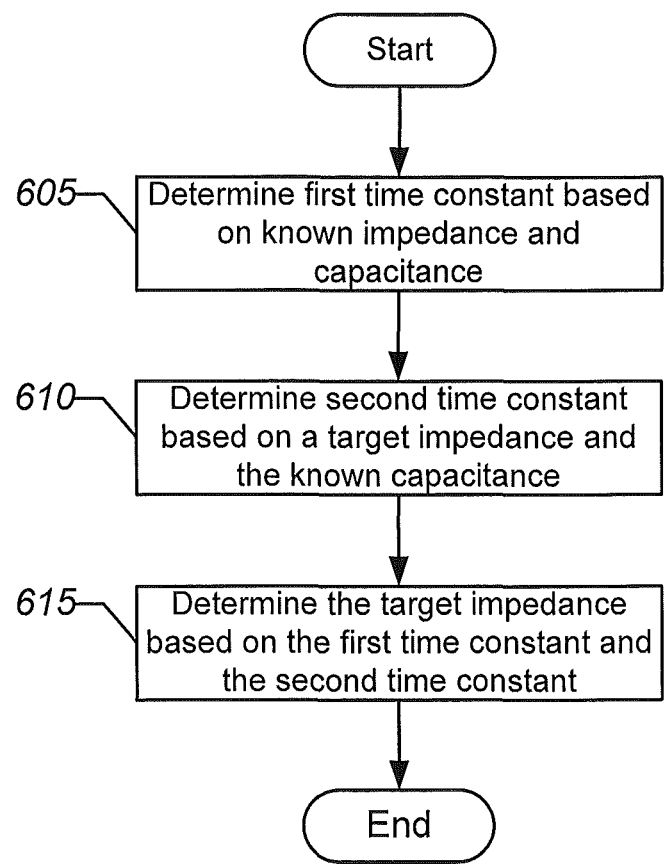
FIG. 6 is a flow chart that illustrates operations for measuring a target impedance according to some embodiments of the present invention.

FIG. 6 is a flow chart that illustrates operations for measuring a target impedance according to some embodiments of the present invention. Operations begin at block 605 where a first time constant is determined based on a known impedance and capacitance, such as capacitor C1 and impedance Z1 described above with respect to FIG. 5. A second time constant based on a target impedance, whose value is unknown, and the known capacitor, such as capacitor C1 and impedance Z2 described above with respect to FIG. 5, is determined at block 610. The target impedance may be determined at block 615 based on the first time constant and the second time constant. In particular, the target impedance value Z2 may be determined according to the following formula:

$$Z2=(T2*Z1)/T1,$$

where T2 is the second time constant and T1 is the first time constant.

Thus, embodiments of the present invention may allow a technician to determine an unknown impedance value, which may be very high, without the need to use a high voltage, which may be dangerous or even disallowed due to safety regulations. Due to the low voltage requirements, the impedance test circuit, according to some embodiments of the present invention, may be applied to simple hand-held devices that could allow technicians to conduct field testing of components. With isolation relays, the test circuitry, according to some embodiments of the present invention, may be added to various types of instruments where a resistance check between a probe and ground or other reference point could provide additional quality assurance checks to the data reliability. Applications include, but are not limited to, testing triboelectric probes used for particulate monitoring of a gas stream to ensure they are properly electrically isolated; testing probes/sensors that detect the levels of materials in hoppers or silos to ensure that dust and debris have not created electrical paths, shorts, and the like that corrupt the electrical signals generated from the probes/ sensors; and generally any application where an impedance verification of an electrical components is desired for quality assurance purposes. The impedance test circuit, according to some embodiments of the present invention, may also be incorporated into electronic devices, computers, embedded systems, and the like for monitoring dust build-up and debris accumulation, particularly in environmentally unfriendly conditions.

Many variations and modifications can be made to the embodiments without substantially departing from the principles of the present invention. All such variations and modifications are intended to be included herein within the scope of the present invention, as set forth in the following claims.

That which is claimed:

1. A method of measuring impedance, comprising:
   determining a first time constant based on a known impedance and a capacitor;
   determining a second time constant based on a target impedance and the capacitor; and
   determining a value of the target impedance based on the first time constant and the second time constant;
   wherein determining the first time constant comprises driving a test circuit with a first test voltage, the test circuit comprising the known impedance and the capacitor connected in series;
   wherein determining the second time constant comprises:
      replacing the known impedance in the test circuit with the target impedance; and
      driving the test circuit with a second test voltage, the test circuit comprising the target impedance and the capacitor connected in series;
   wherein the target impedance comprises an electrical path between a triboelectric probe and a common node; and
   wherein the triboelectric probe is disposed in a gas stream containing particulate matter.

2. The method of claim 1, wherein the first test voltage is in a range from about 0V to about 3.3V.

3. The method of claim 1, wherein the known impedance has a value in a range from 1 megaohm to 10 megaohms.

4. The method of claim 1, wherein the capacitor has a value in a range from 1 nanofarad to 10 nanofarads.

5. The method of claim 1, wherein determining the first time constant further comprises:
   charging the capacitor with the first test voltage; and
   determining a time taken to charge the capacitor to a threshold voltage level.

6. The method of claim 1, wherein determining the first time constant further comprises:
   charging the capacitor to a known voltage level;
   discharging the capacitor through the known impedance; and
   determining a time taken for the capacitor voltage level to decrease to a threshold voltage level.

7. The method of claim 1, wherein the first and second test voltages are the same.

8. The method of claim 1, wherein the first and second test voltages are different.

9. The method of claim 1, wherein the second test voltage is in a range from 0V to 24V.

10. The method of claim 1, wherein the target impedance has a value in a range from 10 megaohms to 50 megaohms.

11. The method of claim 1, wherein determining the second time constant further comprises:
    charging the capacitor with the second test voltage; and
    determining a time taken to charge the capacitor to a threshold voltage level.

12. The method of claim 1, wherein determining the second time constant further comprises:
    charging the capacitor to a known voltage level;
    discharging the capacitor through the target impedance; and
    determining a time taken for the capacitor voltage level to decrease to a threshold voltage level.

13. An impedance measurement circuit, comprising:
    a test circuit comprising a capacitor connected to a test voltage; and
    a controller that is to switch a known impedance in series with the capacitor and the test voltage to determine a first time constant based on the known impedance and the capacitor, to a target impedance in series with the capacitor in place of the known impedance to determine a second time constant based on the target impedance and the capacitor, and to determine a value of the target impedance based on the first time constant and the second time constant;
    wherein the controller is to drive a test circuit with a first test voltage, the test circuit comprising the known impedance and the capacitor connected in series to determine the first time constant;
    wherein the controller is to replace the known impedance in the test circuit with the target impedance and to drive the test circuit with a second test voltage, the test circuit comprising the target impedance and the capacitor connected in series to determine the second time constant;
    wherein the target impedance comprises an electrical path between a triboelectric probe and a common node; and
    wherein the triboelectric probe is disposed in a gas stream containing particulate matter.

14. The impedance measurement circuit of claim 13, wherein the controller is to determine the first time constant by charging the capacitor with the test voltage, the impedance measurement circuit further comprising:
    a voltage comparator that is to determine when the capacitor is charged to a threshold voltage level; and
    a timer that is to determine a time taken to charge the capacitor to the threshold voltage level.

15. The impedance measurement circuit of claim 13, wherein the controller is to determine the second time constant by charging the capacitor with the test voltage, the impedance measurement circuit further comprising: a voltage comparator that is to determine when the capacitor is charged to a threshold voltage level; and
    a timer that is to determine a time taken to charge the capacitor to the threshold voltage level.

16. A computer program product for measuring an impedance, comprising:
    a non-transitory computer readable medium comprising computer readable program code embodied in the medium that when executed by a processor causes the processor to perform operations comprising:
    determining a first time constant based on a known impedance and a capacitor;
    determining a second time constant based on a target impedance and the capacitor; and
    determining a value of the target impedance based on the first time constant and the second time constant;
    wherein determining the first time constant comprises driving a test circuit with a first test voltage, the test circuit comprising the known impedance and the capacitor connected in series;
    wherein determining the second time constant comprises:

replacing the known impedance in the test circuit with the target impedance; and driving the test circuit with a second test voltage, the test circuit comprising the target impedance and the capacitor connected in series;

wherein the target impedance comprises an electrical path between a triboelectric probe and a common node; and wherein the triboelectric probe is disposed in a gas stream containing particulate matter.

* * * * *